(12) United States Patent
Forsberg

(10) Patent No.: US 11,475,795 B2
(45) Date of Patent: Oct. 18, 2022

(54) TRAINING DEVICE

(71) Applicant: SHL Medical AG, Zug (CH)

(72) Inventor: Robert Forsberg, Årsta (SE)

(73) Assignee: SHL MEDICAL AG, Zug (CH)

( * ) Notice: Subject to any disclaimer, the term of this patent is extended or adjusted under 35 U.S.C. 154(b) by 774 days.

(21) Appl. No.: 16/467,648

(22) PCT Filed: Nov. 14, 2017

(86) PCT No.: PCT/EP2017/079206
§ 371 (c)(1),
(2) Date: Jun. 7, 2019

(87) PCT Pub. No.: WO2018/104011
PCT Pub. Date: Jun. 14, 2018

(65) Prior Publication Data
US 2019/0362652 A1    Nov. 28, 2019

(30) Foreign Application Priority Data

Dec. 7, 2016    (EP) .................................... 16202610

(51) Int. Cl.
*G08B 29/12* (2006.01)
*G09B 23/28* (2006.01)

(52) U.S. Cl.
CPC ..... *G09B 23/285* (2013.01); *A61M 2205/581* (2013.01); *A61M 2205/582* (2013.01)

(58) Field of Classification Search
USPC ... 340/515, 516–517, 539.1, 539.22, 539.12, 340/566, 568.1, 582, 691.2, 691.3, 691.6,
(Continued)

(56) References Cited

U.S. PATENT DOCUMENTS

| 4,640,686 A | 2/1987 | Dalling et al. |
| 2007/0111175 A1 | 5/2007 | Raven et al. |

(Continued)

FOREIGN PATENT DOCUMENTS

| CH | 709126 A2 | 7/2015 |
| CN | 101198366 A | 6/2008 |

(Continued)

OTHER PUBLICATIONS

Search report issued in Taiwanese Patent Application No. 106140505 dated Sep. 13, 2018.

(Continued)

*Primary Examiner* — Daniel Previl
(74) *Attorney, Agent, or Firm* — McDonnell Boehnen Hulbert & Berghoff LLP

(57) ABSTRACT

A training device (10) for simulating a mechanical function of a medicament delivery device, which training device (10) comprises a dummy housing (20), a first element (52) comprising an actuator (70), a second element (58) comprising an indication member (60), and wherein a relative movement of the first element (52) towards the second element (58), which movement exceeds at least a distance D, causes the actuator (70) to interact with the indication member (60) such that a feedback signal is generated for indicating to a user that a simulated mechanical function has occurred.

20 Claims, 5 Drawing Sheets

(58) Field of Classification Search
USPC .......................................... 340/693.8, 825.24
See application file for complete search history.

(56) References Cited

U.S. PATENT DOCUMENTS

| | | | |
|---|---|---|---|
| 2008/0059133 A1* | 3/2008 | Edwards | A61M 15/009 703/7 |
| 2013/0266919 A1* | 10/2013 | Baker | G09B 19/00 434/262 |
| 2014/0128843 A1* | 5/2014 | Baker | A61M 5/31583 604/211 |
| 2014/0309616 A1* | 10/2014 | Edwards | A61M 15/00 434/262 |
| 2014/0311210 A1* | 10/2014 | Rounds | G01N 19/02 73/9 |
| 2014/0350468 A1* | 11/2014 | Cordes | A61M 5/31566 604/131 |

FOREIGN PATENT DOCUMENTS

| | | |
|---|---|---|
| CN | 102646355 A | 8/2012 |
| CN | 103635948 A | 3/2014 |
| CN | 104272367 A | 1/2015 |
| CN | 105900162 A | 8/2016 |
| WO | 2013032389 A1 | 3/2013 |
| WO | 2013130973 A1 | 9/2013 |
| WO | 2014056868 A1 | 4/2014 |
| WO | 2014139914 A1 | 9/2014 |
| WO | 2016078870 A1 | 5/2016 |

OTHER PUBLICATIONS

English Translation of Abstract of Swiss Patent Application No. 709126 dated Jun. 6, 2019.

* cited by examiner

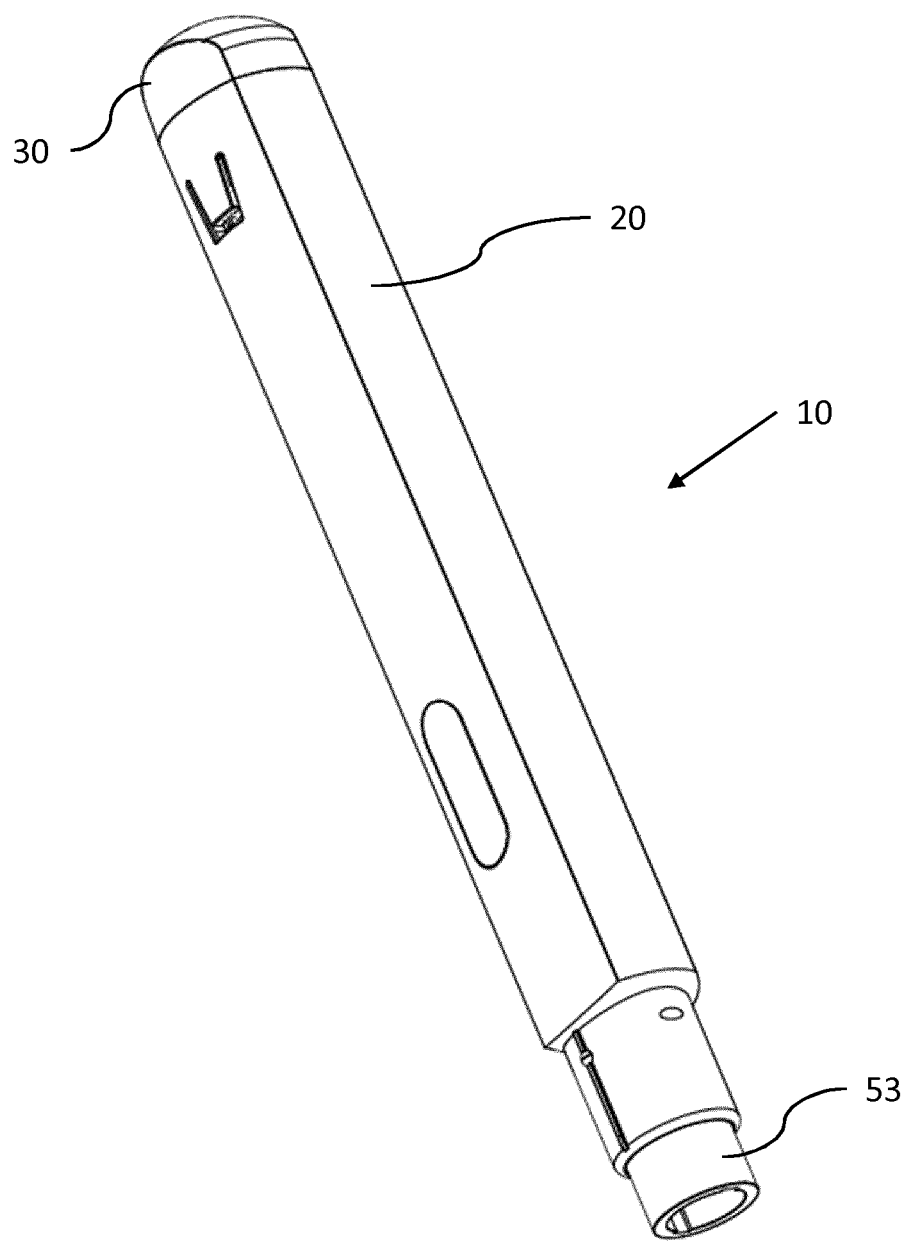
Fig. 2
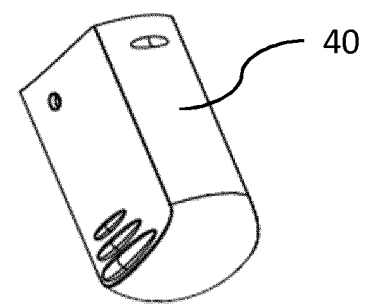

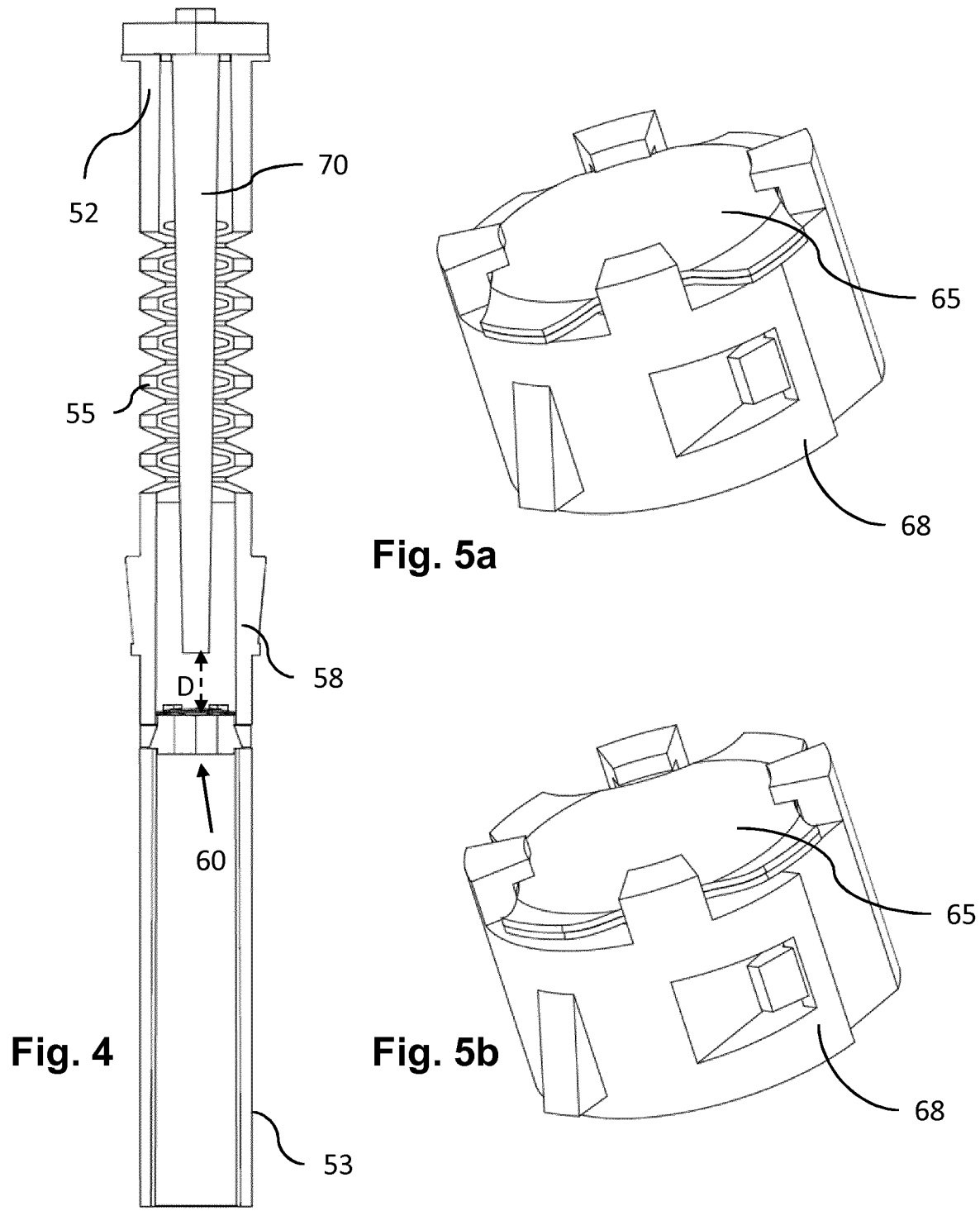

TRAINING DEVICE

CROSS REFERENCE TO RELATED APPLICATIONS

The present application is a U.S. National Phase Application pursuant to 35 U.S.C. § 371 of International Application No. PCT/EP2017/079206 filed Nov. 14, 2017, which claims priority to European Patent Application No. 16202610.8 filed Dec. 7, 2016. The entire disclosure contents of these applications are hereby incorporated by reference into the present application.

TECHNICAL FIELD

The present device relates to a training device for simulating a mechanical function of a medicament delivery device. In more particular, the device indicates to a user that a simulated mechanical function has occurred.

BACKGROUND

Medicament delivery devices such as auto-injectors provide allow users to handle medicament delivery in an easy, safe and reliable manner, without the need of a physician.

An auto-injector currently on the market is disclosed in WO2013032389 A1. This document discloses an injection device comprising a housing and a container holder arranged within the housing. The container holder is configured to accommodate a medicament container having a needle attached to one end thereof and a stopper sealingly and slidably arranged inside the medicament container at the other end thereof. The injection device also has a first and a second energy accumulating member arranged in the interior of the housing and adapted to accumulate and store energy, a sleeve that is slidably arranged in relation to the housing, and a plunger holder arranged to be connected to the container holder. The plunger holder is operationally associated with the first energy accumulating member such that due to an output axial force from the first energy accumulating member, the plunger holder and the container holder are axially moveable in relation to the housing a predetermined distance towards the proximal end of the injection device from an initial position to a position following needle penetration. The injection device also includes a plunger rod being arranged with a proximal end thereof contactable with the stopper and slidably arranged in relation to the plunger holder and to the container holder. The plunger rod is operationally associated with the second energy accumulating member such that due to an output axial force from the second energy accumulating member the plunger rod is axially moveable in relation to the container holder towards the proximal end of the injection device from a locked position to a position following medicament injection, wherein, in the initial position of the plunger holder, movement of the plunger holder towards the proximal end of the injection device is substantially inhibited by at least one first biasable member interacting with the plunger holder, the first biasable member recoiling when being overlapped by an opening and/or recess of the sleeve such that the plunger holder is released. The injection device is in particular suitable for emergency applications such as adrenaline injections, as it has an auto-penetration and auto-injection functionality.

Before a user commences a drug administration programme by means of an auto-injector, it may be valuable for the user to undergo training to learn how to administer a drug properly by means of a particular auto-injector. A training device may be used for this purpose. Training is especially important for users of emergency devices, so that the user knows how to use it, and does not hesitate, when in a stressful situation.

SUMMARY

In view of the above, a general object of the present disclosure is to provide a training device for simulating a mechanical function of a medicament delivery device. Such a function may be a start of penetration and/or injection.

In the present disclosure, when the term "distal" is used, this refers to the direction pointing away from the dose delivery site. When the term "distal part/end" is used, this refers to the part/end of the delivery device, or the parts/ends of the members thereof, which under use of the medicament delivery device is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which under use of the medicament delivery device is/are located closest to the dose delivery site.

Further, the term "longitudinal", with or without "axis", refers to a direction or an axis through the device or components thereof in the direction of the longest extension of the device or the component.

The term "lateral", with or without "axis", refers to a direction or an axis through the device or components thereof in the direction of the broadest extension of the device or the component. "Lateral" may also refer to a position to the side of a "longitudinally" elongated body.

In a similar manner, the terms "radial" or "transversal", with or without "axis", refers to a direction or an axis through the device or components thereof in a direction generally perpendicular to the longitudinal direction, e.g. "radially outward" would refer to a direction pointing away from the longitudinal axis.

Also, if nothing else is stated, in the following description wherein the mechanical structure of the device and the mechanical interconnection of its components is described, the device is in an initial non-activated or non-operated state.

According to a main aspect of the present disclosure there is provided a training device for simulating a mechanical function of a medicament delivery device, which training device comprises a dummy housing, a first element comprising an actuator, and a second element comprising an indication member wherein a relative movement of the first element towards the second element, which movement exceeds at least a distance D, causes the actuator to interact with the indication member such that a feedback signal is generated for indicating to a user that a simulated mechanical function has occurred.

Advantageously, the dummy housing resembles the actual device for which the user needs training. The first element and the second element are movable relative to each other. One element may resemble a needle guard, movable in relation to the housing and in relation to the other element, and the other element may be arranged inside the housing, or may resemble an activation button protruding through the housing. The user may then simulate a medicament delivery by pressing the needle guard against a delivery site. The element resembling the needle guard may then move the distance D and thereby cause an interaction between the actuator and the indication element such that the feedback signal is generated. Alternatively, the first and the second element may both move, such as if the one of the elements resembles a needle guard, and the other element resembles a button, so that the sum of the distances moved by both elements towards each other exceeds the distance D.

According to another aspect of the present disclosure, the feedback signal is an audible and/or tactile signal.

In order to mimic an activation of a function, an audible and/or tactile signal is generated. For instance, the movement of a container and its needle during an auto-penetration step may often be both heard and felt in a real delivery device. Therefore, the generated signal of the training device should preferably be similar to the real device.

According to another aspect of the present disclosure, the first element and the second element are integrated in a unitary component and wherein the unitary component comprises a resilient member which separates the first element and the second element such that the first element and the second element are spring-biased away from each other.

Training devices are preferably inexpensive devices that are offered for free, or sold at low prices, to users of medicament delivery devices. To lower manufacturing costs, and to simplify assembly, the unitary component may be molded to comprise the first and second elements, as well as a resilient member to spring-bias the elements away from each other.

Alternatively, the first and second elements may be stand-alone components that are assembled separately and wherein a spring is added to bias the elements away from each other.

According to another aspect of the present disclosure, the actuator is a longitudinally elongated member.

According to another aspect of the present disclosure, the actuator is a proximally directed pin.

According to another aspect of the present disclosure, the actuator is fixedly attached to, or integrated with, the first element.

In this manner, if the first element moves, the actuator moves together with the first element towards the second element for interacting with the indication member.

According to another aspect of the present disclosure, the indication member comprises a resiliently flexible member.

According to another aspect of the present disclosure, the indication member comprises a metal snap dome.

The flexing of the indication member may cause a tactile or audible signal, and the metal snap dome in particular is known for this effect from the field of tactile metal switch contacts.

According to another aspect of the present disclosure, the indication member is fixedly attached to, or integrated with, the second element.

As such, if the second element moves, the indication member may move together with the second element towards the first element and its actuator.

According to another aspect of the present disclosure, the indication member is arranged with an electric circuit, an energy source, a switch, a speaker unit and/or a piezoelectric unit, for generating the feedback signal.

According to another aspect of the present disclosure, the electric circuit further comprises a control unit, having a clock function.

According to another aspect of the present disclosure, the control unit measures the duration of a simulated dose delivery and compares it with a predetermined time value, and controls the feedback signal to indicate to the user the occurrence of a correct simulated dose delivery or a failed simulated dose delivery.

To further improve the quality of the feedback given to the user, the electronic circuit may be arranged to not only indicate the start of needle penetration and/or dose delivery, but may also indicate to the user the time needed to press the training device against the training injection site.

According to another aspect of the present disclosure, the second element is distally movable relative to the housing, against a spring bias, towards the first element.

According to another aspect of the present disclosure, the second element comprises a dummy needle guard and the first element is fixed to the housing.

Thus, the dummy needle guard extends proximally from a proximal end of the dummy housing. The first element is concealed inside the housing. In this case, the first element replaces the drive mechanism with which a real needle guard interacts in the medicament delivery device that is simulated.

According to another aspect of the present disclosure, the simulated mechanical function is a start of needle penetration and/or a start of delivery of a dose of medicament, and/or a duration of a simulated dose delivery.

For an emergency device, it is important for the user to know the steps that have to be completed to cause a dose delivery. Emergency delivery devices are normally highly automated. Therefore, the user has normally completed the necessary steps when the needle penetration and/or the dose delivery commences. The generated feedback signal will tell the user of the training device that the device has been handled correctly.

According to an alternative aspect of the present disclosure, the actuator is a distally directed pin and the first element is distally movable, against a spring bias, towards the second element. The first element comprises a dummy needle guard and the second element is fixed to the housing.

The actuator may be comprised by the first element, which may comprise the dummy needle guard.

According to an alternative aspect of the present disclosure, the actuator is a distally directed pin and the second element is proximally movable, against a spring bias, towards the first element. The second element comprises a dummy activation button and the first element is fixed to the housing.

This alternative aspect simulates a device which is only activated by a button, for instance a medicament delivery device that lacks a needle guard. Therefore, the indication member is movable with the dummy activation button.

According to an alternative aspect of the present disclosure, the actuator is a proximally directed pin and the first element is proximally movable, against a spring bias, towards the second element. The first element comprises a dummy activation button and the second element is fixed to the housing.

This alternative aspect simulates a device which is only activated by a button, for instance a medicament delivery device that lacks a needle guard. Therefore, the actuator is movable with the dummy activation button.

According to an alternative aspect of the present disclosure, the actuator is a proximally directed pin and the first element is proximally movable and the second element is distally movable, the first and the second element being individually movable against a spring bias, towards each other. The first element comprises a dummy activation button and the second element comprises a dummy needle guard.

In this way, the training device may simulate a medicament delivery device that requires movement of both the needle guard and a button to activate needle penetration and/or dose delivery. The proximally directed actuator pin moves with the dummy activation button and the indication member moves with the dummy needle guard.

According to an alternative aspect of the present disclosure, the actuator is a distally directed pin and the first element is distally movable and the second element is proximally movable, the first and the second element being individually movable against a spring bias, towards each other. The first element comprises a dummy needle guard and the second element comprises a dummy activation button.

In this way, the training device may simulate a medicament delivery device that requires movement of both the needle guard and a button to activate needle penetration and/or dose delivery. The distally directed actuator pin moves with the dummy needle guard and the indication member moves with the dummy activation button.

DETAILED DESCRIPTION

Figure 1:
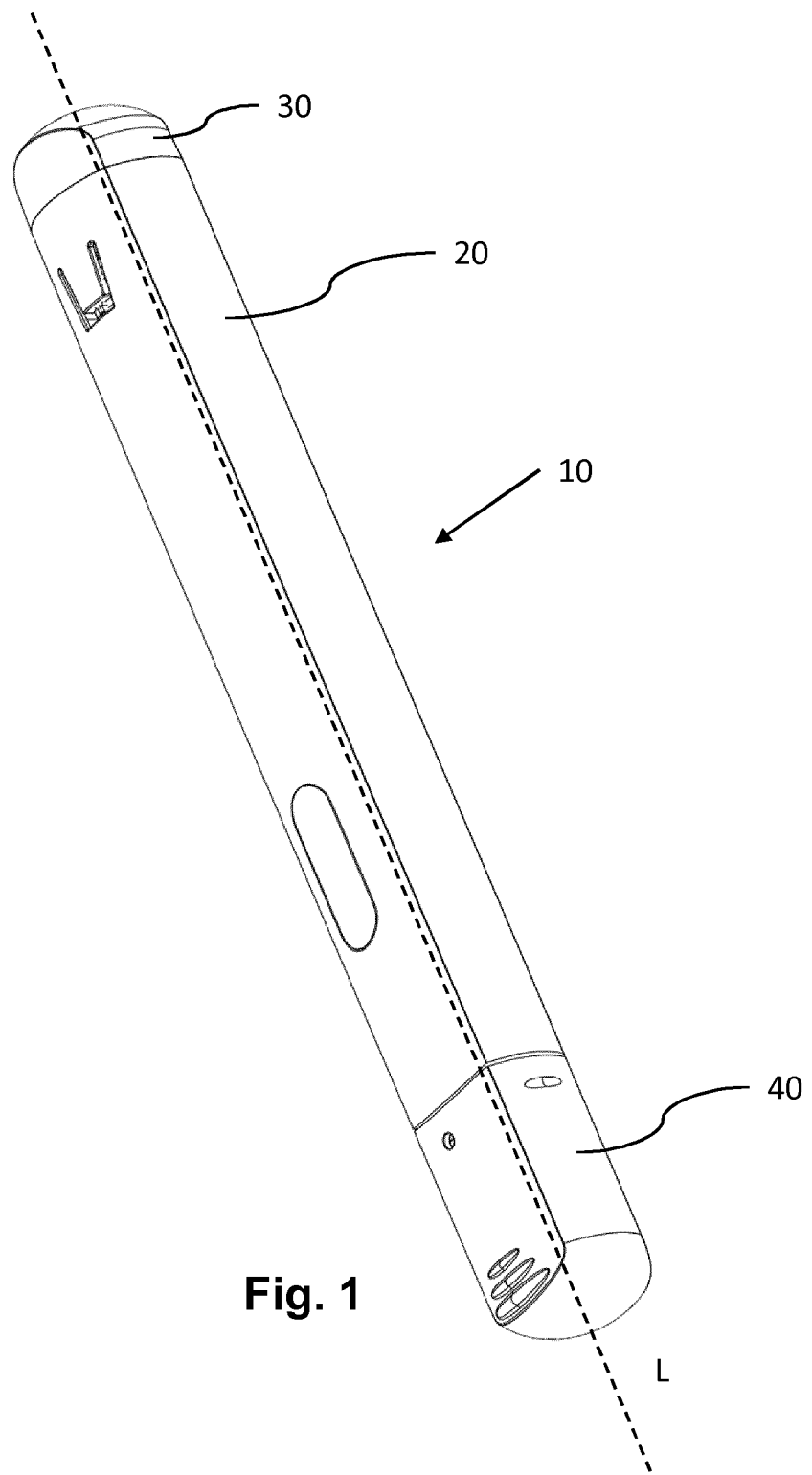
FIG. 1 a perspective view of a training device according to an embodiment of the present disclosure
FIG. 2 a perspective view of a ready state of the training device of FIG. 1
FIG. 3 an exploded perspective view of the training device of FIG. 1
FIG. 4 a cross-section view of a unitary component of the training device
FIG. 5a-b perspective views of different states of the indication member of the training device
FIG. 6a-b concepts of an electric circuit according to an alternative embodiment of the present disclosure

FIG. 1 shows a training device 10, which is preferably designed to resemble a real medicament delivery device for which the user needs training. The training device 10 is elongated along an axis L. The training device 10 comprises a dummy housing 20, a distal end cap 30 and a proximal removable cap 40. In the embodiment shown in FIG. 1, the end cap 30 is fixedly attached to the housing 20, but it is conceivable that end cap 30 may instead be replaced by a movable dummy activation button, should the training device be designed to mimic a medicament delivery device having an activation button. The end cap 30 could also be integrated with the housing 20, but for manufacturing purposes, the end cap 30 is preferably an individual component that is fixedly attached to the housing 20 during assembly.

FIG. 2 shows the training device 10 in a ready state, in which state the proximal cap 40 has been removed and the training device 10 is ready to be used. A dummy needle guard 53 protrudes proximally from the housing.

Figure 3:
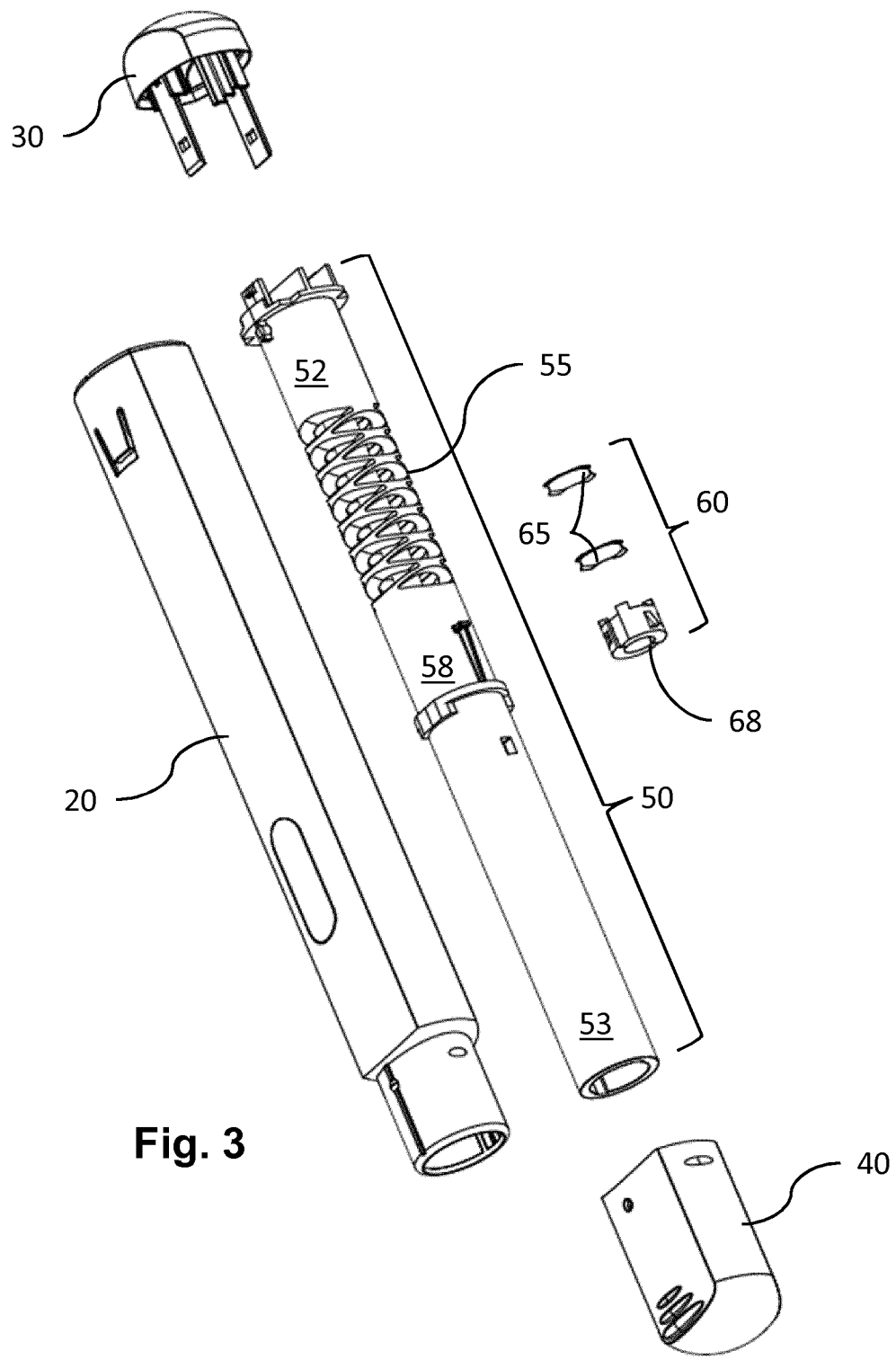

FIG. 3 displays an exploded view of the training device 10. A unitary component 50, of a generally tubular shape, is arranged in the housing. The unitary component 50 comprises at its distal end a first element 52, and at its proximal end a second element 58. The first element 52 and the second element 58 are axially directly connected, but separated, by a resilient member 55 such that the first element 52 and the second element 58 are spring-biased away from each other.

The first element 52, the second element 58 and the resilient member 55 could also be arranged as individual components, but a unitary component 50, comprising the three members, is preferred for manufacturing and assembly purposes since the component may be molded, and mounted in the housing 20 in one piece.

The first element 52 and the second element 58 are movable in relation to each other. The relative mobility of the first element 52 and the second element 58 may mean that they are both movable relative to each other and relative to the housing 20. In another embodiment, one of the elements may be movable relative to the housing, e.g. towards the other element, while the latter is fixed relative to the housing.

In the ready state shown in FIG. 2, the dummy needle guard 53 protrudes proximally from a proximal end of the housing 20. The first element 52 of the unitary component 50 is fixedly attached to the housing 20. The second element 58 of the unitary component 50 is axially movable towards the first component. In the ready state, the resilient member 55 is in a relaxed state. Movement of the second element 58 towards the first element 52 tensions the resilient member 55. The movement of the second element 58 towards the first element 52 therefore requires the application of a certain force to overcome a spring force of the resilient member 55. The force is applied by the user pushing the dummy needle guard 53 of the device against a training injection site.

The first element 52 comprises an actuator 70 (FIG. 4), and the second element 58 comprises an indication member 60. The actuator 70 is configured to mechanically interact with the indication member 60 as they come into contact with each other. The actuator 70 and the indication member 60 may be configured in a number of ways, as a skilled person sees fit. The actuator 70 may be fixedly attached to, or integrated with, the first element 52, and may be a longitudinally elongated member, such as a rod. In the exemplified embodiment the actuator 70 is a proximally directed rod. The indication member 60 may be fixedly attached to, or integrated with, the second element 58, and may comprise a holder 68 and a resiliently flexible member, such as a metal snap dome 65. In the embodiment shown in FIGS. 3-5, the indication member comprises two metal snap domes 65. The holder 68 is configured to hold the metal snap dome, or domes, in a fixed position relative to the second element 58.

FIGS. 3 and 4 show the first element 52 as a distal part of the unitary member 50, and the second element 58 as a proximal part of the unitary member 50. However, in alternative embodiments, the first and the second elements may switch positions, for instance such that the actuator 70 is distally directed towards the indication member 60.

A metal snap dome is a dome-shaped metal plate. Upon application of a sufficient force to the dome 65, the dome will suddenly buckle to the shape of an inverted dome 65'. The sudden buckling will emit a click sound and a person applying the force to the dome will feel a tactile sensation as the dome buckles. Upon removal of the force, the metal snap dome 65 will resume its original shape.

In the ready state, the actuator 70 and the indication member 60 are separated from each other by distance D (FIG. 4). When the relative movement of the first element 52 and the second element 58 toward each other equals or exceeds the distance D, the actuator 70 and the indication member 60 interact, by mechanical contact. The actuator 70 is configured to apply a force to the indication member 60. The applied force causes the metal snap dome 65 to buckle, as described above, such that a feedback signal is generated for indicating to a user that a simulated mechanical function has occurred. The feedback signal indicates that the user has handled the training device correctly, and if the training device had been a real medicament delivery device, an automatic sequence would have been triggered to cause a needle penetration and/or a delivery of a dose of medicament. The feedback signal may be an audible and/or tactile signal, such as, but not limited to, a click or a slight impact.

FIG. 5a shows a detailed view of the indication member 60, comprising the holder 68 and two metal snap domes 65 in an unbuckled state.

FIG. 5b shows a detailed view of the indication member 60 of FIG. 5a, wherein a force has been applied to the metal snap domes 65, which force has caused the metal snap dome 65 to buckle into the shape of an inverted dome 65', i.e. to a buckled state.

The resilient member 55 is configured to mimic the resilience of a mechanical function, or spring, of a real medicament delivery device. Furthermore, the resilience of the indication member 60 may be configured by selecting a suitable thickness of the metal snap dome 65, or by using one or more metal snap domes 65 in the holder 68.

In an alternative embodiment, the holder 68 of the indication member 60 may further be arranged with an electric circuit 80, an energy source 82, such as a battery, a switch 84, a speaker unit 86 and/or a piezoelectric unit 88. The electric circuit 80 may further comprise a control unit 90, having a clock function. The electric circuit 80 is conceptualized in FIGS. 6a and 6b.

Figure 6A:
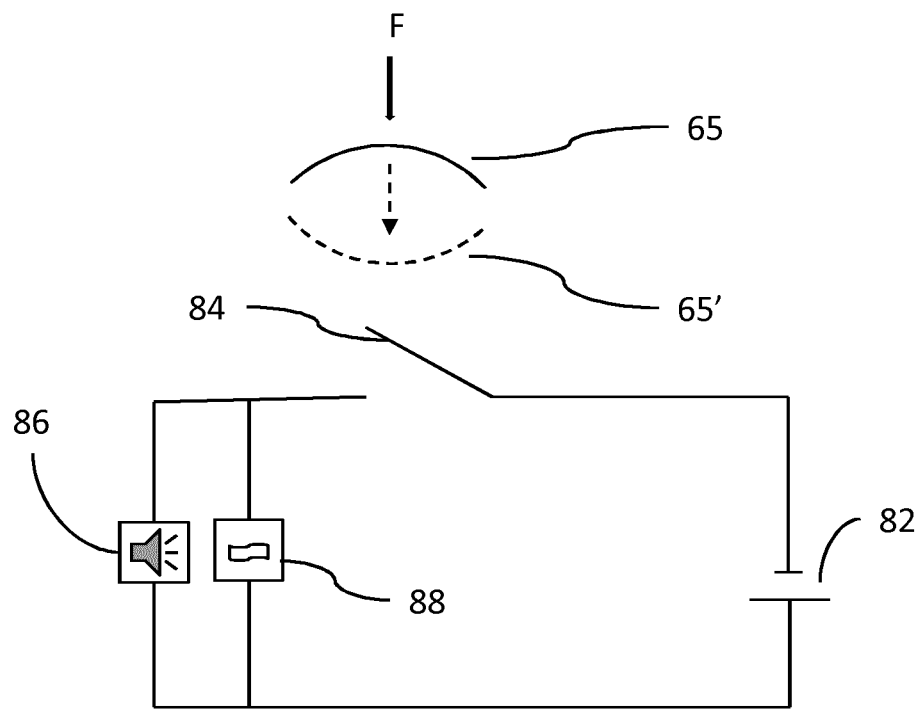
Figure 6B:
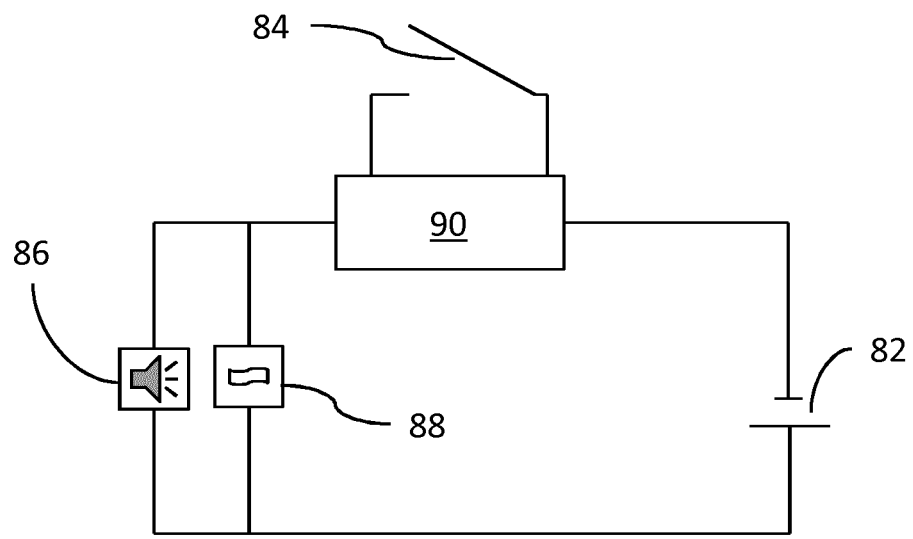

In the alternative embodiment shown in FIG. 6a, the buckling of the metal snap dome 65 causes the inverted dome 65' to close the switch 84 such that the electric circuit 80 is activated. The feedback signal may be an electronic sound, emitted by the speaker 86, and/or a vibration caused by the piezoelectric element 88 of the electric circuit 80. Alternatively, as shown in FIG. 6b, the electric circuit 80 may also comprise a control unit 90 having a clock function, which control unit may be activated by the switch 84. The control unit 90 measures the duration of a simulated dose delivery and compares it with a predetermined time value, and controls the feedback signal to indicate to the user the occurrence of a correct simulated dose delivery, or of a failed simulated dose delivery. The duration of the simulated dose delivery means the duration that the user presses the training device 10 against the training injection site such that the metal snap dome remains in the shape of the inverted dome 65'. The control unit 90 may activate a sound and/or a vibration for the duration of a simulated medicament dose delivery. The control unit 90 may further generate a negative signal if the training device 10 is removed from the simulated injection site before the duration of the simulated dose delivery has reached the predetermined time value, such as if the user removes the training device from the training injection site too early. The control unit 90 may further generate a positive signal if the training device 10 is pressed against the training injection site for a longer duration than the predetermined time value. The predetermined time value is the time it takes for the real medicament delivery device to deliver a dose.

The speaker element 86 and the piezoelectric element 88 shown in FIGS. 6a and 6b should be regarded as complementary or optional elements. According to preference, either the speaker element 86 or the piezoelectric element 88, or both, may be comprised by the electric circuit.

In use, the training device 10 is supplied in the state shown in FIG. 1. The user removes the cap 40 and pushes the training device, i.e. the projecting dummy needle guard 53, against a training injection site. In the exemplified embodiment, the dummy needle guard 53 is a part of the second element 58 and the first element 52 is fixedly attached to the housing 20. Therefore, the second element 58 moves in relation to the housing 20, against the spring bias of the resilient member 55, towards the first element 52. When the second element has moved the distance D, metal snap dome 65 of the indication member 60 makes contact with the actuator 70. If the user applies enough force, which force is calculated to match the force required for the corresponding real medicament delivery device, the metal snap dome 65 will buckle and emit an audible sound and/or a tactile sensation. In the case of the alternative embodiment described above, the control unit 90 and its clock function may further control the feedback signal to maintain the signal for the duration of the simulated dose delivery, i.e. for the duration of the user pressing the device against the training injection site. The control unit 90 may also generate feedback signals to indicate to the user that the force and the training device 10 was applied for a sufficient time, or that the user removed the training device 10 too early.

After the simulated dose delivery, the user may remove the device from the training injection site, whereupon the second element 58 and the dummy needle guard 53 will return to the original position of the ready state, shown in FIG. 2.

The invention claimed is:

1. A training device for simulating a mechanical function of a medicament delivery device, which training device comprises
    a dummy housing;
    a first element comprising an actuator having a proximal end, where the actuator is axially fixed relative to the first element and is axially movable within and relative to the dummy housing;
    a second element comprising an indication member having a distal end separated from the proximal end of the actuator by a distance D, where the indication member is axially fixed relative to the second element and is axially movable relative to the dummy housing;
    wherein a mechanical interaction between the proximal end of the actuator and the distal end of the indication member occurs when there is a relative moment of the first element towards the second element a distance greater than or equal to the distance D, where the mechanical interaction generates a feedback signal indicating to a user that a simulated mechanical function has occurred.

2. The training device according to claim 1,
    wherein the feedback signal is an audible and/or tactile signal.

3. The training device according to claim 2,
    wherein the first element and the second element are integrated in a unitary tubular component and
    wherein a resilient member is positioned in the tubular unitary component and separates the first element from the second element such that the first element and the second element are spring-biased away from each other.

4. The training device for the medicament delivery device according to claim 1,
    wherein the actuator is a longitudinally elongated member.

5. The training device according to claim 4,
    wherein the actuator is a proximally directed rod.

6. The training device according to claim 5,
    wherein the second element is distally movable relative to the housing, against a spring bias, towards the first element.

7. The training device according to claim 4,
    wherein the actuator is fixedly attached to, or integrated with, the first element.

8. The training device according to claim 1,
wherein the indication member comprises a resiliently flexible member.

9. The training device according to claim 8,
wherein the resiliently flexible member is a metal snap dome.

10. The training device according to claim 1,
wherein the indication member is fixedly attached to, or integrated with, the second element.

11. The training device according to claim 1,
wherein the indication member is arranged with an electric circuit, and energy source, a switch, a speaker unit and/or a piezoelectric unit, for generating the feedback signal.

12. The training device according to claim 11,
wherein the electric circuit further comprises a control unit, having a clock function.

13. The training device according to claim 12,
wherein the control unit is able to generate a negative signal, if the training device is removed from a simulated injection site before the duration of the simulated dose delivery has reached the predetermined time value and generate a positive signal, if the training device has been pressed against the training injection site for a long duration than the predetermined time.

14. The training device according to claim 11,
wherein the control unit measures a duration of a simulated dose delivery and compares it with a predetermined time value, and
controls the feedback signal to indicate to the user the occurrence of a correct simulated dose delivery, or of a failed simulated dose delivery.

15. The training device according to claim 14,
wherein the second element comprises a dummy needle guard and the first element is fixed to the housing.

16. The training device according to claim 15,
wherein the dummy needle guard is part of the second element.

17. The training device according to claim 16,
wherein the first element is fixedly attached to the housing.

18. The training device according to claim 1,
wherein the simulated mechanical function is a start of needle penetration.

19. The training device according to claim 1,
wherein the simulated mechanical function is a start of delivery of a dose medicament.

20. The training device according to claim 1,
wherein the simulated mechanical function is a duration of a simulated dose delivery.

* * * * *